United States Patent [19]
Lemole

[11] Patent Number: 5,342,375
[45] Date of Patent: Aug. 30, 1994

[54] NEEDLE GRIPPING APPARATUS

[76] Inventor: Gerald M. Lemole, 404 Tomlinson Rd., Huntingdon Valley, Pa. 19006

[21] Appl. No.: 9,624

[22] Filed: Jan. 27, 1993

[51] Int. Cl.⁵ .............................................. A61B 17/00
[52] U.S. Cl. ................................. 606/148; 606/139; 606/211
[58] Field of Search ............... 606/106, 127, 139, 144, 606/147, 148, 205, 207, 209–211

[56] References Cited

U.S. PATENT DOCUMENTS

| | | |
|---|---|---|
| 644,932 | 3/1900 | Miller . |
| 1,422,538 | 7/1922 | Cameron . |
| 1,464,807 | 8/1923 | Clark . |
| 2,413,142 | 12/1946 | Jones et al. . |
| 2,416,260 | 2/1947 | Karle . |
| 2,601,513 | 6/1952 | Gladstone . |
| 2,623,152 | 12/1952 | Ammon . |
| 2,631,585 | 3/1953 | Siebrandt . |
| 2,723,666 | 11/1955 | Greenberg ........................ 606/205 |
| 2,743,726 | 5/1956 | Grieshaber . |
| 2,818,866 | 1/1958 | Thomas . |
| 2,897,820 | 8/1959 | Tauber . |
| 3,140,715 | 7/1964 | Whitton, Jr. et al. . |
| 3,367,337 | 2/1968 | Gavna et al. . |
| 3,500,829 | 3/1970 | Abramowitz . |
| 3,503,398 | 3/1970 | Fogarty et al. ................... 606/207 |
| 3,511,242 | 5/1970 | Agnone . |
| 3,577,991 | 5/1971 | Wilkinson . |
| 3,878,848 | 4/1975 | Hiebert . |
| 4,300,564 | 11/1981 | Furihata . |
| 4,312,337 | 1/1982 | Donohue . |
| 4,320,760 | 3/1982 | Sun et al. . |
| 4,350,151 | 9/1982 | Scott ................................ 606/147 |
| 4,357,302 | 11/1982 | Giroir . |
| 4,457,756 | 7/1984 | Kern et al. . |
| 4,724,838 | 2/1988 | Hasson . |
| 4,834,090 | 5/1989 | Moore . |
| 4,955,896 | 9/1990 | Freeman . |
| 5,002,561 | 3/1991 | Fisher ............................... 606/205 |
| 5,019,091 | 5/1991 | Porat et al. . |
| 5,047,046 | 9/1991 | Bodoia . |
| 5,047,049 | 9/1991 | Sali . |
| 5,129,912 | 7/1992 | Noda et al. ....................... 606/148 |
| 5,147,373 | 9/1992 | Ferzli ................................ 606/207 |
| 5,201,743 | 4/1993 | Haber et al. ..................... 606/147 |
| 5,250,072 | 10/1993 | Jain ................................... 606/205 |

Primary Examiner—Stephen C. Pellegrino
Assistant Examiner—J. A. Schmidt
Attorney, Agent, or Firm—Seidel, Gonda, Lavorgna & Monaco

[57] ABSTRACT

The present invention provides an apparatus which is designed to capture, and manipulate the movement of, surgical needles as they pass through the tissue wall of a patient. The apparatus of the present invention has, among other things, a removable gripping body component which is designed to rest against the tissue wall of a patient. This gripping body component has sufficient resistance to be penetrated by, and grip, the needle's point. The apparatus also has a component which is designed to manipulate the movement of the gripping body component. This manipulating component has a ledge surface or opening defined thereon or therein. The apparatus also has a fastening component. At least one end of the fastening component is secured to the gripping component. The fastening component is designed to secure the removable gripping component to the manipulating component. The fastening component includes a flexible and resilient latching member which can move from an engaging position to a disengaging position with respect to the manipulating component's ledge or opening.

16 Claims, 5 Drawing Sheets

NEEDLE GRIPPING APPARATUS

FIELD OF THE INVENTION

This invention relates in general to medical instruments. More particularly, it relates to hand held medical instruments which are designed to grip, and manipulate the movement of, the pointed end portion of a surgical needle as the surgical needle passes through the tissue wall of a patient.

BACKGROUND OF THE INVENTION

As is well known, the cutting and sewing of tissue are two important aspects of surgery. With respect to the sewing of tissue, a vast array of needle and suturing devices are available. These devices, however, have been basically unchanged since the introduction of the modern needle holder and curved needle.

There are basic stitch movements involved in most surgical sewing procedures. These basic movements are as follows: gripping the shank portion of a needle with a needle holder, manipulating the needle holder to push the pointed end portion of the needle at least partly through the tissue, disengaging the shank portion of the needle from the needle holder, gripping the pointed end portion of the needle with a suitable gripping means, pulling the needle and the suture completely through the tissue, supporting the needle with a suitable means (e.g., fingers, forceps, etc.), regripping the shank portion of the needle with the needle holder and repeating the procedure as necessary.

Although these steps have been used for many decades, there are problems associated therewith. For example, due to the inherent sharpness of the pointed end portion of the needle, extreme care has to be used when gripping the needle as it is passing through the tissue. Specifically, if the gripping means is the thumb and forefinger of a medical practitioner, the needle may puncture these appendages. This is of major concern to both the practitioner and the patient especially with the growing awareness of the means by which the AIDS virus can be transmitted. Notwithstanding the potential problems associated with the implementation of this gripping procedure, many practitioners still use it.

In an attempt to remedy this problem, some medical practitioners use a forceps-type apparatus to grip the pointed end portion of the needle. Although this approach keeps the practitioner's fingers from coming in direct contact with the needle's point, there are still problems associated therewith. For example, the use of a forceps has been known to dull and/or etch barb-like protrusions on the pointed end portion of a needle. This complicates the suturing process.

Over the years, there have been other attempts to improve the manner by which a needle's point is gripped as it passes through a patient's tissue. One of these attempts is disclosed in U.S. Pat. No. 3,511,242 (henceforth the '242 patent). Specifically the '242 patent discloses a surgical finger cot having a hollow flexible body adapted for receiving a finger therein. On at least one side of this flexible body, there is a relatively stiff "ear" which protrudes tangentially therefrom. This protruding ear, which has a well-defined terminal edge, is designed to provide a back-up for the needle's point as it passes through the patient's tissue.

Although the purpose of the ears disclosed in the '242 patent is to protect a medical practitioner's finger from the needle's point, the practitioner's fingers may still be punctured if extreme care is not used. Specifically, the surface area of the ears is relatively small when compared to the surface area of the unprotected finger in the finger cot. Therefore, the margin of error allowed, when guessing exactly where the needle's point will emerge from the patient's tissue is also relatively small. Accordingly, if the practitioner makes a slight miscalculation as to the location of the needle's point while it is under the tissue being sewn, there is a high probability that the practitioner's finger will be punctured.

Another problem associated with the needle gripping means disclosed in the '242 patent pertains to the fact that it is physically attached to the practitioner's finger via the finger cot. This phenomena limits the implementation of such a gripping means since it can be used only where the practitioner's finger can reach. Such a limitation is significant since it prohibits the employment of this gripping means with certain types of surgical procedures (e.g., endoscopic surgical procedures).

U.S. Pat. No. 3,878,848 (henceforth the '848 patent) discloses another attempt to improve the manner in which a needle's point is gripped as it passes through a patient's tissue. In the '848 patent, a surgical needle capturing device is disclosed which includes a "body member" having sufficient stiffness to be penetrated by a needle's point as it passes through a patient's tissue. This body member serves a similar purpose as the "ears" which were disclosed in the '242 patent.

One major differences between the approach disclosed in the '848 patent and that disclosed in the '242 patent is that, in the approach disclosed in the '848 patent, the body member is secured to a "handle member" which is, itself, attached to a "manipulating element". While this difference affords the approach disclosed in the '848 patent a greater range of use, there are still significant limitations associated therewith.

For example, in the device disclosed in the '848 patent, the body member is formed around a bifurcation or U-shaped extension defined at one end of the handle member. This is the only means by which these two components are attached to one another. Accordingly, a medical practitioner cannot be certain if, and/or when, the two will separate from one another.

The possibility of the two separating from one another is of great concern to the medical profession. For example, if the two separate while the device is being used to capture a needle being employed in an endoscopic surgical procedure, the obvious consequences can be catastrophic and even fatal.

In the past decade, the number and frequency of endoscopic surgical procedures has increased significantly. As surgical instruments become more refined, those in the medical profession expect these numbers to continue growing. Also in the past decade, the concern for protecting medical practitioners from being infected by, and/or transmitting, the AIDS virus has increased significantly.

Notwithstanding the events which have taken place in the past decade, the means employed by medical practitioners to grip the pointed end portion of a needle still remain unchanged. Therefore, there is an immediate need for an improved method for gripping the pointed end portion of a surgical needle as it passes through a patient's tissue.

SUMMARY OF THE INVENTION

One object of this invention is to provide an apparatus which captures, and manipulates the movement of, a surgical needle passing through the tissue of a patient.

Another object of this invention is to provide an apparatus which can capture, and manipulate the movement of, a surgical needle employed in an endoscopic surgical procedure.

A further object of this invention is to provide a apparatus which includes, among other things, a way to fasten a removable needle point gripping means to a manipulating means.

These and other objects are achieved through the advent of a novel apparatus which is designed to capture, and manipulate the movement of, a surgical needle as it passes through the tissue wall of a patient. The apparatus of the present invention includes, among other things, a removable gripping means which is designed to rest against the tissue wall of a patient. This gripping means has sufficient resistance to be penetrated by, and grip, the pointed end portion of a surgical needle.

This novel apparatus also includes a manipulating means. The manipulating means is designed to control the movement of the apparatus's removable gripping means.

Also included in this novel apparatus is a latching member. The latching member is designed to secure the removable gripping means to the manipulating means. The latching member is flexible and resilient. Moreover, it has at least one end which is fixedly secured to the gripping means. The latching member is designed to interlock with a ledge surface or opening defined in the manipulating means.

Other objects, aspects and advantages of the present invention will become apparent to those skilled in the art upon reading the following detailed description when considered in connection with the accompanying drawings and appended claims.

BRIEF DESCRIPTION OF THE DRAWINGS

A more complete appreciation of the invention, and many attendant advantages thereof, will be readily obtained as the same becomes better understood by referring to the following detailed description, when considered in connection with the accompanying figures briefly described below.

DETAILED DESCRIPTION OF THE INVENTION

Figure 1:
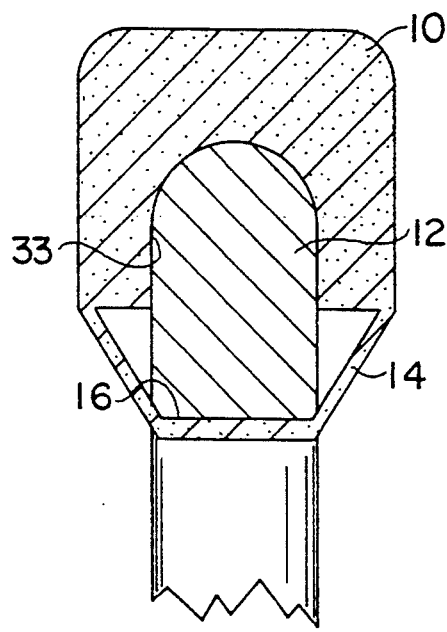
FIGS. 1–3 are cross-sectional views showing different embodiments of an apparatus designed to capture, and manipulate the movement of, a surgical needle in accordance with the present invention.

The present invention pertains to hand held medical instruments which are designed to grip, and manipulate the movement of, the pointed end portion of a surgical needle as the surgical needle passes through the tissue wall of a patient. This novel suture gripping apparatus includes, among other things, a removable gripping means which is designed to rest against the tissue wall of a patient. This gripping means has sufficient resistance to be penetrated by, and grip, the pointed end portion of a surgical needle.

The gripping means is made from a material which can be penetrated by a needle's point. The gripping means is made from a material such that, once the point of the needle passes into its body portion, the material exerts a pressure thereon which is greater than that exerted on the shank portion of the needle by the tissue being sutured. Consequently, the needle can be drawn through the tissue by moving the suture gripping apparatus disclosed herein.

Any suitable material which has the aforementioned features can be employed as the gripping means of the present invention. Preferably, the gripping means is made from a sterilizable, rubber-like material. Examples of materials from which a suitable gripping means can be made are silicon and/or other materials having properties similar thereto.

The novel apparatus also includes a manipulating means. The manipulating means is designed to control the movement of the apparatus's removable gripping means.

The manipulating means can be a handle dedicated as a component of a suture gripping apparatus. The manipulating means can also be any conventional surgical tool which inherently has, or was modified to include, a ledge or an opening which can accept a latching member. This latching member, and it relationship to the ledge and/or opening of the manipulating means will be discussed later in more detail.

Another characteristic of the apparatus's manipulating means is that it should be sterilizable. Moreover, since the gripping means is removable, the manipulating means need not necessarily be made from an inexpensive, disposable material. To the contrary, it can be made from a material which can be reused; thus, reducing long term costs.

As indicated above, the apparatus's gripping means is removable. However, to insure that the gripping means does not come off unexpectedly, the suture gripping apparatus of the present invention also includes a means of securely fastening it to the manipulating means. This is accomplished by a latching member.

In accordance with the present invention, the latching member is flexible and resilient and has at least one end fixedly secured to the gripping means. The latching member is designed to interlock with a ledge surface or opening defined in the manipulating means.

The particular location, size and configuration of the opening or ledge depends, in part, upon the particular latching member being employed. Generally, the opening is located in close proximity to the gripping means.

As stated above, the latching member is comprised of a flexible and resilient material. This enables it to be moved from an engaged position to a disengaged position.

In addition to being flexible and resilient, the material from which the latching member is made must also be sterilizable and able to withstand pressures exerted thereon during normal suturing procedures. For example, the latching member can be made from metal, metal alloy, polymeric materials, and/or a combination thereof. The preferred material from which the latching member can be made depends, in part, on the composition of the gripping means and the specific surgical procedure in which the suture gripping apparatus is to be employed. It is also within the purview of this invention for the latching member to be made from the same material as the gripping means. An example of this is illustrated in FIG. 1.

Figure 2:
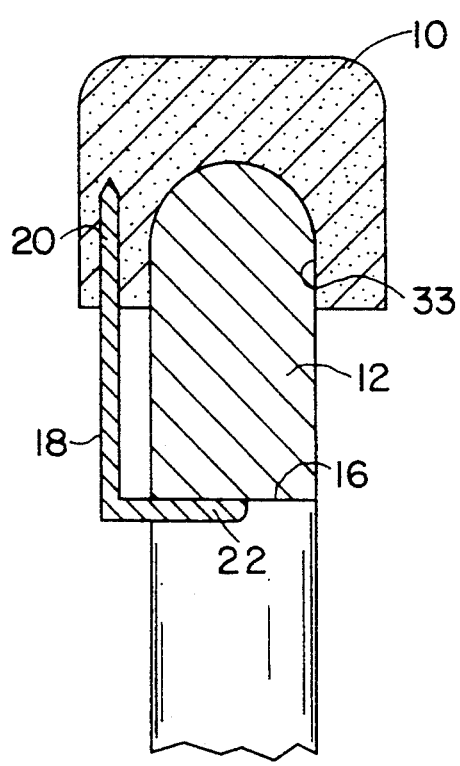
Figure 3:
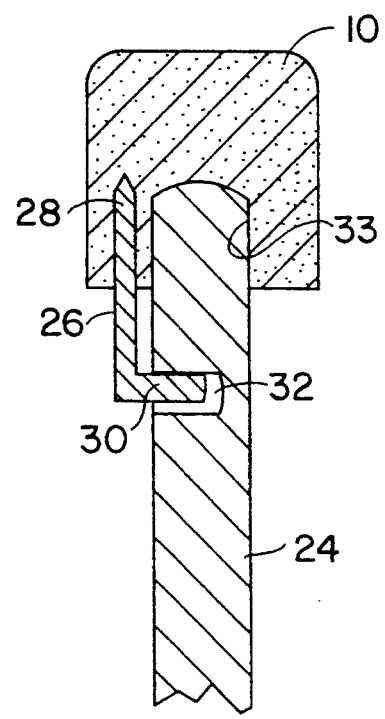

FIGS. 1–3 show three specific examples of how a removable gripping means can be secured to a manipulating means in accordance with the present invention. These are merely examples and should not be construed as limiting.

In FIG. 1, the gripping means 10 is secured to the manipulating means 12 via latching member 14. Both ends of latching member 14 are attached to gripping means 10; thus, forming a loop. A similar configuration can also be seen in FIGS. 6, 7 and 8 which will be discussed later.

The latching member of FIG. 1 is engaged with the ledge 16 defined in manipulating means 12. Ledge 16 could have been inherently present in manipulating means 12 (See, for example, FIGS. 6, 7 and 8) or could have been placed there for the specific purpose of engaging latching member 14 (not shown).

FIG. 2 shows another method of engaging a gripping means to a manipulating means via a latching member. Specifically, in FIG. 2, gripping means 10 is secured to manipulating means 12 via latching member 18. A first end 20 of latching member 18 is embedded into gripping means 10. Preferably, latching member's end 20 is screwed into or permanently bonded to gripping means 10.

The second end 22 of latching member 18 is hook-shaped. In FIG. 2, hooked-shaped end 22 is designed to correspond to and engage with the ledge 16 defined in manipulating means 12. As with FIG. 1, ledge 16 could have been inherently present in manipulating means 12 (see, for example, FIG. 4) or could have been placed there for the specific purpose of engaging latching member 18 (not shown).

FIG. 3 shows yet another method of engaging a gripping means to a manipulating means via a latching member. Specifically, in FIG. 3, gripping means 10 is secured to manipulating means 24 via latching member 26.

As with FIG. 2, latching member 26 also has a first end 28 which is embedded into gripping means 10. Moreover, the second end 30 of latching member 26 is also hook-shaped. However, the major difference between FIGS. 2 and 3 is that, in that, in FIG. 3, latching member 26 is designed to engage and/or fit into opening 32 defined in manipulating means 24. As with FIGS. 1 and 2, opening 32 could have been inherently present in manipulating means 24 (not shown) or could have been placed there for the specific purpose of engaging latching member 18 (see, for example, FIGS. 5, 9 and 10).

In all of the embodiments illustrated above, the latching members must be flexible and resilient. The degree of flexibility and resiliency associated with the latching members must be such that it permits the repeated engagement and disengagement of the gripping means and the manipulating means. However, it must also be able to keep the gripping means and manipulating means securely fastened together during suturing procedures.

However, since at least one end of the latching member is attached to the gripping means, and since the gripping means has a degree of flexibility and resiliency associated therewith, at least some of the flexibility and resiliency necessary to move the latching member from the engaged position to the disengaged position can be obtained from the gripping means. Therefore, when determining the minimum degree of flexibility and resiliency which the latching member must have in order that the invention may be practiced as indicated herein, one should take into consideration the gripping means' flexibility and resiliency, and the location and manner in which the latching member and gripping means are secured to one another.

Moreover, in each of the above embodiments, there is a divot 33 at the point where the gripping means contacts the manipulating means. Divot 33 can be specifically designed in the gripping means, or it can be formed by the downward pressure exerted by the latching member when it is in an engaged position. Preferably, at least some of the divot is caused by the latching member's downward pressure.

FIGS. 4–8 illustrate specific embodiments of the invention wherein the manipulating means is a forceps. In each of these Figures the forceps is identified as item 50 and the gripping means is identified as item 51. An inherent feature of forceps 50 is a ledge 52 (shown in phantom) created at the apex where legs 54 and 56 meet.

Figure 4:
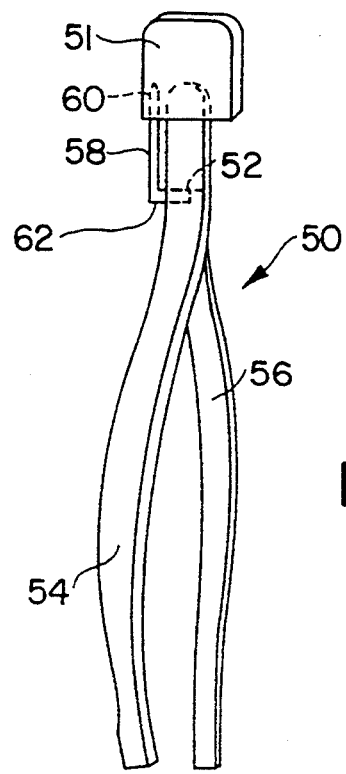
FIG. 4 is a perspective view showing one embodiment of a suture gripping apparatus in accordance with the present invention.

In FIG. 4, latching member 58 has a first end 60 (shown in phantom) embedded in gripping means 51 and a hook-shaped end 62 engaged with ledge 52. For a similar embodiment of this configuration, see FIG. 2.

Figure 5:
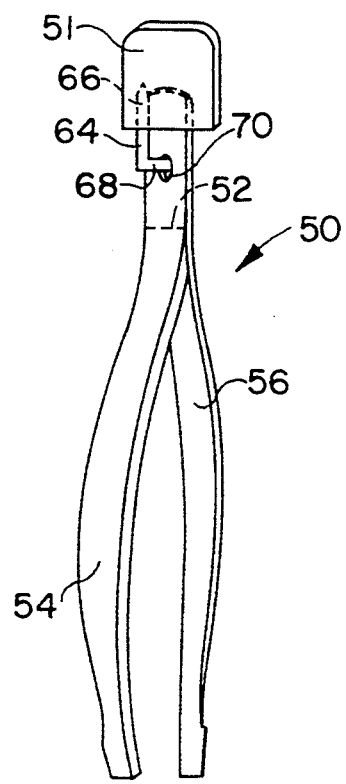
FIG. 5 is a perspective view showing another embodiment of a suture gripping apparatus in accordance with the present invention.

In FIG. 5, latching member 64 also has a first end 66 (shown in phantom) embedded in gripping means 51 and a hooked-shaped end 68. However, instead of engaging ledge 52, hook-shaped end 68 of latching member 64 is designed to fit into an opening 70 defined in forceps 50. For similar embodiments of this configuration, see FIGS. 3, 9 and 10.

Figure 6:
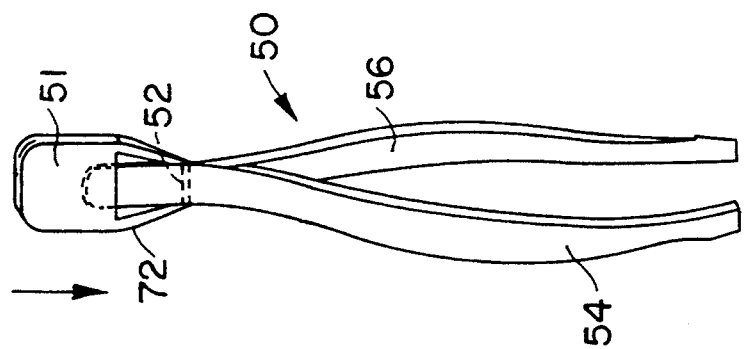
FIGS. 6, 7 and 8 are perspective views illustrating a method of fastening a gripping means to a manipulating means in accordance with the present invention.
Figure 7:
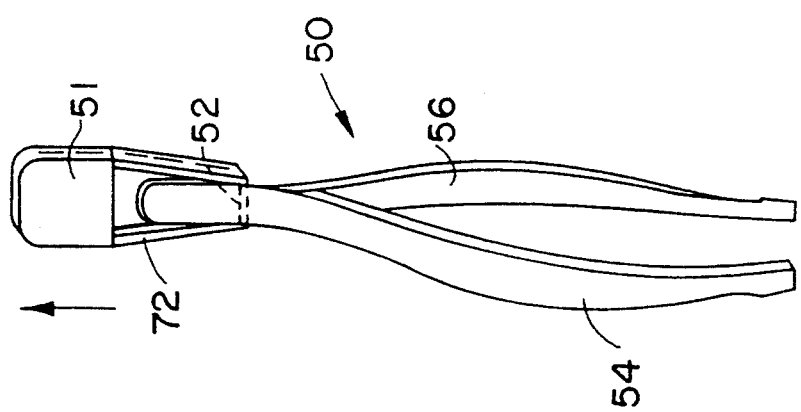
Figure 8:
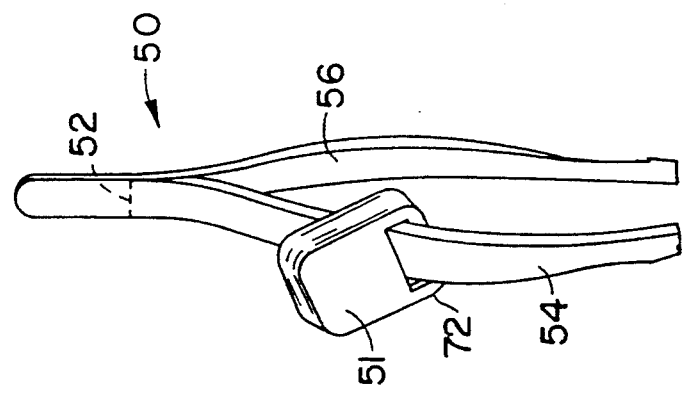

FIGS. 6–8 not only show yet another method of fastening a gripping means to a forceps in accordance with the present invention; but also, they show how to fasten that specific gripping means thereto. As can be seen in FIGS. 6–8, both ends of latching member 72 are attached to gripping means 51; thus, creating a loop. Forceps leg 54 is passed through the loop (FIG. 6) until latching member 72 engages forceps ledge 52.

Latching member 72 is then stretched by pulling gripping means 51 (FIG. 7). After gripping means is positioned over the upper end of forceps 50, latching member 72 is permitted to at least partially relax (FIG. 8). For a similar embodiment, see FIG. 1.

When practicing this invention, it is preferred to have the latching member designed such that there is at least some positive tension between it and the manipulating means' ledge and/or opening when the two are engaged. Moreover, as an added assurance that the gripping means will not become separated from the manipulating means during a suturing procedure, it is also within the purview of this invention to have a means of locking the latching member in place after it has engaged the manipulating means ledge and/or opening (not shown).

Figure 9:
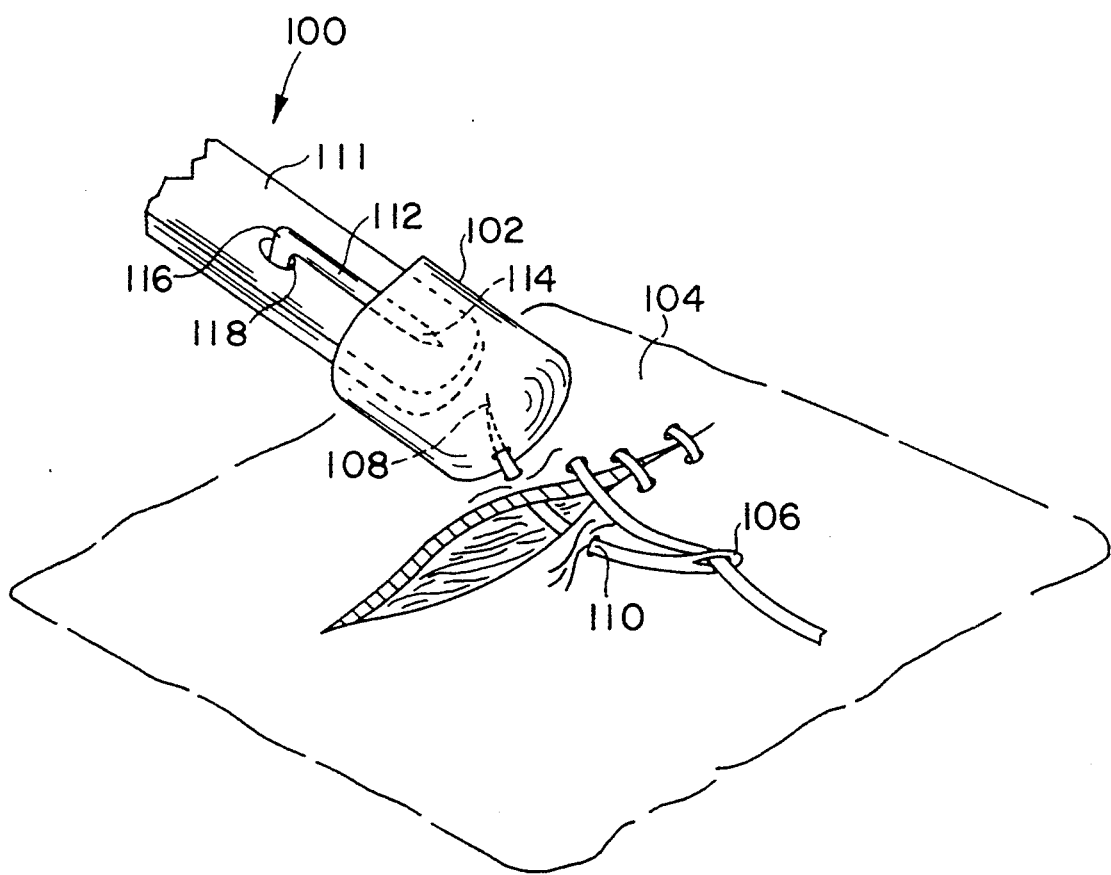
FIG. 9 is a perspective view showing the use of one embodiment of a suture gripping apparatus designed in accordance with the present invention.
Figure 10:
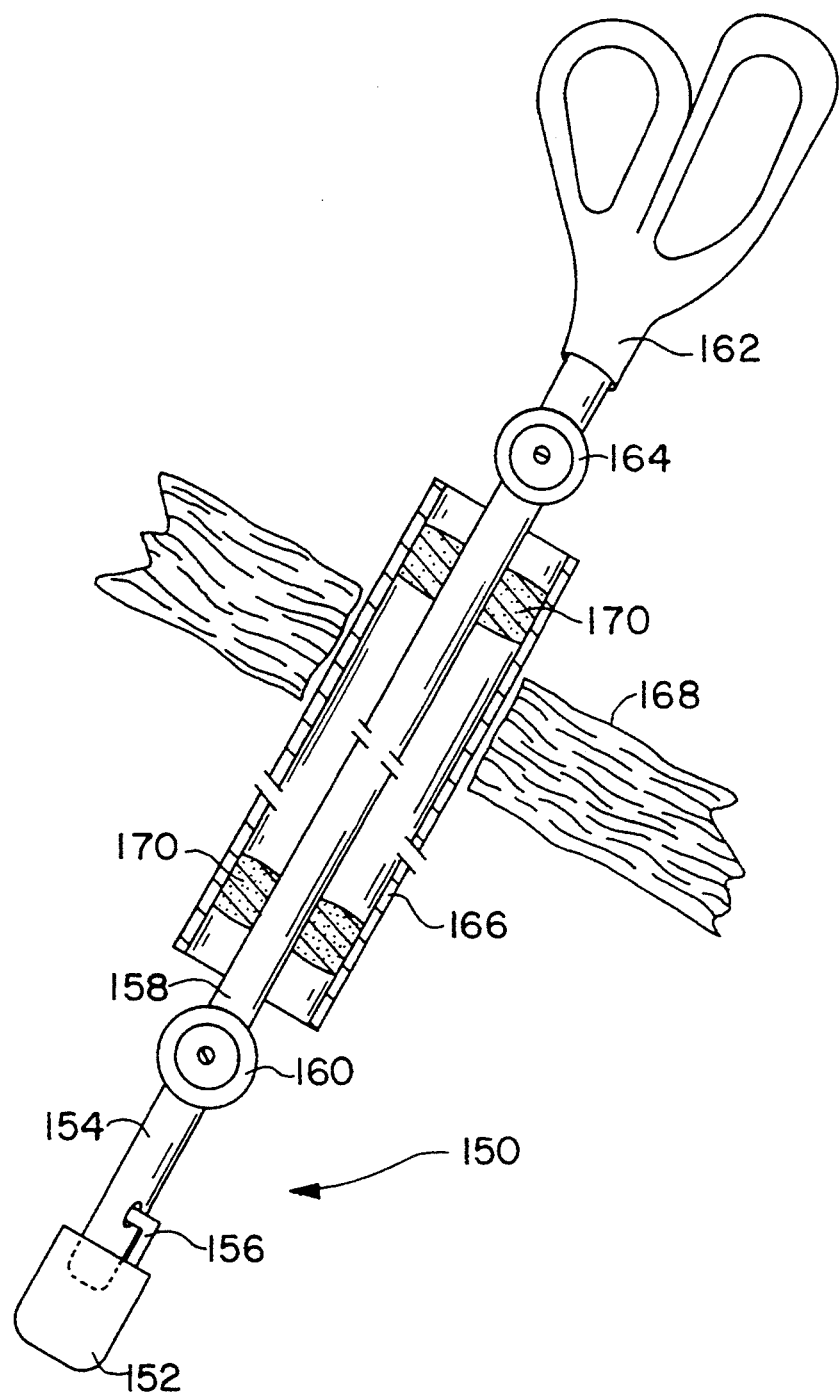
FIG. 10 is a partially perspective and partially cross-sectional view of one embodiment of a suture gripping apparatus designed for use in an endoscopic surgical procedure.

Examples of ways in which the suture gripping apparatus of the present invention can be employed are illustrated in FIGS. 9 and 10. These are merely examples of possible uses.

Referring now to FIG. 9, the suture gripping apparatus illustrated therein is defined generally as item 100. In operation, the apparatus' gripping means 102 is pressed against a patient's tissue wall 104 which is to be sutured. The surgical needle 106 is pushed through the tissue until its pointed end portion 108 penetrates the surface of and becomes embedded into gripping means 102.

Due to its resiliency, gripping means 102 grips the needle's pointed end portion 108 (shown in phantom) with a tension which is greater than that exerted by the tissue on the needle's shank portion 110. Accordingly, by manipulating gripping means 102 with the handle 111, needle 106 can be drawn through the patient's tissue.

With this invention, the practitioner no longer has to be concerned of the possibility that gripping means 102 might separate from handle 111 during a suturing procedure. Specifically, one of the novel features on this invention is the inclusion of a latching member. In FIG. 9, the latching member is represented as item 112.

Latching member 112 has a first end 114 (shown in phantom) which is embedded into gripping means 102. A second end 116 of latching member 112 is interlocked with a corresponding opening 118 defined in handle 111.

Without the implementation of a latching member as disclosed herein, the possibility exists that the gripping means will separate from the manipulating means during a surgical procedure. This can have dire consequences especially if the procedure is being performed endoscopically.

In addition to providing added safety as described above, the latching member of the present invention also reduces the long-term cost of surgical equipment, as well as the possibility of cross contamination. Specifically, since this latching member can be moved from an engaged to a disengaged position, after each surgical procedure the gripping means can be disengaged from the handle (i.e., the manipulating means) and discarded. This is an important feature since it reduces the chance of contamination while keeping down costs since it is not necessary to replace the entire suture gripping apparatus.

While the suture gripping apparatus of the present invention can be used in most suturing procedures, it is especially useful in those procedures which are performed endoscopically. As used herein, an endoscopic surgical procedure is one performed on an internal body part or organ through the use of tubes and an instrument which can visualize the internal part or organ (i.e., an endoscope).

Due to the nature of endoscopic surgical procedures, the suture gripping apparatus of choice has had a forceps-type gripping end. This, however, results in the problems set out in the background portion of this disclosure—dulling the needle's point and/or creating barb-like protrusions on the needle's shank portion. Either of these occurrences complicates the surgical procedure. Although the medical industry is aware of suture gripping apparatuses such as that disclosed in U.S. Pat. No. 3,878,848, supra, their use is limited due to the possibility of the gripping means becoming separated from the handle.

One specific embodiment of this invention provides, for the first time, a suture gripping apparatus which can be safely used in endoscopic surgical procedures. This novel apparatus on not only overcomes the problems associated with conventional forceps-type gripping apparatuses; but also, it avoids the potential problems associated with gripping apparatuses such as that disclosed in the '848 patent.

One possible form this novel apparatus can take is illustrated in FIG. 10. As with all gripping apparatuses of this invention, the apparatus 150 has a gripping means 152, a manipulating means 154 and a latching member 156. Since suture gripping apparatus 150 is designed for endoscopic surgical procedures, it is attached to extension tube 158 via hinge 160.

The distal end of extension tube 158 is connected to a movement control means 162 via hinge 164. Movement control means 162 is interconnected with manipulating means 154 such that angling control means 162 with respect to extension tube 158 results in an angular movement of manipulating means 154.

Endoscopic suture gripping apparatus 150 is designed to have its suture gripping end portion fit through a conduit 166 which passes through the patient's skin 168. If desired, gasket-type material 170 can be positioned between the outer wall of extension tube 158 and the inner wall of conduit 166. This will minimize the potential of contamination while providing a slight resistance to aid in making precise movements and manipulations.

There are many types of endoscopic apparatuses known in the industry. Upon reading this disclosure, those skilled in the art will be able to adapt this invention thereto.

It is evident from the foregoing that various modifications can be made to the embodiments of this invention without departing from the spirit and scope thereof. These modifications, and the embodiments resulting therefrom, will be apparent to those skilled in the art after reading this disclosure. Having thus described the invention, it is claimed as follows.

That which is claimed is:

1. An apparatus for capturing, and manipulating the movement of, a surgical needle passing through the tissue wall of a patient, said apparatus comprises:

(a) a removable gripping means, said gripping means being designed to slide onto and off of a means for manipulating the movement of the gripping means in a controlled manner, said gripping means being designed to rest against a portion of a patient's tissue wall, and said gripping means being comprised of a material which can be penetrated by, and grip, the pointed end portion of a surgical needle, after the needle's pointed end portion passes through said tissue wall, (b) a means for manipulating said removable gripping means in a controlled manner, said manipulating means having a ledge surface or an opening defined thereon or therein, and (c) a latching member designed to permit said removable gripping means to be secured to, and removed from said manipulating means, wherein one end of said latching member is embedded into said removable gripping means, and wherein the other end of said latching member is hook-shaped, said latching member being movable between a locked and an unlocked relationship with said manipulating means' ledge surface or opening, said latching member being comprised of a flexible and resilient material, which is different from that material from which said removable gripping means is made, and said latching member, when in the locked relationship, prevents said gripping means from sliding off of said manipulating means when said gripping means is subjected to the pulling action encountered in a suture gripping procedure, and, when in the unlocked relationship, permits said gripping means to be slid off of said manipulating means when said gripping means is subjected to the pulling action encountered in a suture gripping procedure.

2. An apparatus as recited in claim 1, wherein said removable gripping means comprises a rubber-like material.

3. An apparatus as recited in claim 1, wherein the hook-shaped portion of said latching member is designed to fit into a corresponding opening defined in said manipulating means.

4. An apparatus as recited in claim 1, wherein said manipulating means is a forceps.

5. An apparatus as recited in claim 4, wherein said removable gripping means comprises a rubber-like material.

6. An apparatus as recited in claim 4, wherein the hook-shaped portion of said latching member is designed to fit into a corresponding opening defined in said forceps.

7. An apparatus as recited in claim 1, wherein said manipulating means and said removable gripping means are designed for use in endoscopic surgical procedures by being dimensioned to fit through a tube which has been inserted into a patient's body cavity.

8. An apparatus as recited in claim 7, wherein said removable gripping means comprises a rubber-like material.

9. An apparatus as recited in claim 7, wherein the hook-shaped portion of said latching member is designed to fit into a corresponding opening defined in said manipulating means.

10. An apparatus as recited in claim 7, wherein said manipulating means is connected to an extension tube via a hinge.

11. An apparatus for capturing, and manipulating the movement of, a surgical needle passing through the tissue wall of a patient, said apparatus comprises:

(a) a removable gripping means, said gripping means being designed to slide onto and off of a means for manipulating the movement of the gripping means in a controlled manner, said gripping means being designed to rest against a portion of a patient's tissue wall, and said gripping means being comprised of a material which can be penetrated by, and grip, the pointed end portion of a surgical needle, after the needle'pointed end portion passes through said tissue wall.

(b) a means for manipulating said removable gripping means in a controlled manner, said manipulating means having a ledge surface defined thereon or therein wherein said ledge surface being generally perpendicular to the longitudinal axis of the manipulating means, and (c) a latching member designed to permit said removable gripping means to be secured to, and removed from said manipulating means, wherein both ends of said latching member are attached to said removable gripping means such that a loop is defined, said latching member being movable between a locked and an unlocked relationship with said manipulating means' ledge surface, said latching member being comprised of a flexible and resilient material, and said latching member, when in the locked relationship, prevents said gripping means from sliding off of said manipulating means when said gripping means is subjected to the pulling action encountered in a suture gripping procedure, and, when in the unlocked relationship, permits said gripping means to be slid off of said manipulating means when said gripping means is subjected to the pulling action encountered in a suture gripping procedure.

12. An apparatus as recited in claim 11, wherein the looped latching member is designed to fit around a portion of said manipulating means.

13. An apparatus as recited in claim 11, wherein said manipulating means is a forceps.

14. An apparatus as recited in claim 13, wherein the looped latching member is designed to fit around a portion of said forceps.

15. An apparatus as recited in claim 11, wherein said manipulating means and said removable gripping means are designed to fit through a tube which has been inserted to the body cavity of a patient.

16. An apparatus as recited in claim 15, wherein the looped latching member is designed to fit around a portion of said manipulating means.

* * * * *